United States Patent [19]

Teleha et al.

[11] Patent Number: 5,308,851

[45] Date of Patent: May 3, 1994

[54] BISPYRIDYL-CONTAINING HETEROCYCLES USEFUL FOR TREATING COGNITIVE DISORDERS

[75] Inventors: Christopher A. Teleha, New Castle, Del.; Matthew E. Voss, Lincoln University, Pa.

[73] Assignee: The Du Pont Merck Pharmaceutical Company, Wilmington, Del.

[21] Appl. No.: 70,826

[22] Filed: Jun. 3, 1993

[51] Int. Cl.$^5$ .................. A61K 31/435; C07D 213/00
[52] U.S. Cl. ..................................... 514/333; 546/256
[58] Field of Search ....................... 546/256; 514/333

[56] References Cited

U.S. PATENT DOCUMENTS 4,760,083  7/1988  Meyers et al. ................... 514/333
5,173,489  12/1992  Earl et al. ........................ 514/252

Primary Examiner—C. Warren Ivy
Assistant Examiner—Zinna N. Davis
Attorney, Agent, or Firm—Gildo E. Fato

[57] ABSTRACT

Bispyridyl-containing heterocycles, or pharmaceutically acceptable salts thereof, are useful in treating neurological disorders in mammals. The compounds have efficacy over a broad dosage ranges as measured in both neurotransmitter release assay and by hypoxia induced cognition deficit.

12 Claims, No Drawings

BISPYRIDYL-CONTAINING HETEROCYCLES USEFUL FOR TREATING COGNITIVE DISORDERS

BACKGROUND OF THE INVENTION

1. Field of the Invention

This invention is related to heterocyclic bispyridines, pharmaceutical compositions containing them and methods of using them to treat neurological disorders in mammals.

2. State of the Art

Alzheimer's Disease (AD) and Senile Dementia (SD) are neurological disorders generally characterized by a reduction in cortical cholinergic activity. Neurological disorders may be characterized by altered neurotransmitter function and concomitant cognitive impairment in diseases such as, but not limited to, Alzheimer's Disease, Parkinson's Disease, Pick's Disease, Huntington's Disease, and Age Associated Memory Impairment. This has led to a focus on the basal forebrain cholinergic system as the major source of neurochemical and neuroanatomical substrates mediating age-related memory loss. However, it is very unlikely, given the complexity of the brain, that any single neurotransmitter would selectively and exclusively be involved in a neurological disorder so pervasive as dementia or age-related memory impairment. A growing literature has described multiple neurotransmitter, neuroanatomical and behavioral changes in dementia from varying etiologies. It is, therefore, possible and likely that age-related memory deficits and cognitive impairment resulting from AD and SD involve concurrent changes in several neurotransmitter systems and neurotransmitter replacement therapy should involve multiple systems in the brain.

U.S. Pat. Nos. 4,760,083, issued Jul. 26, 1988, 5,173,489, issued Dec. 22, 1992 all herein incorporated by reference, describe many compounds useful in the treatment of neurological disorders such as Alzheimer's Disease and Senile Dementia. In U.S. Pat. No. 5,173,489, certain thiophene heterocycles, pyrrolo and pyrazole heterocycles are disclosed. While the compounds of the present, invention are similar to, those within the broad scope of application U.S. Pat. No. 5,173,489 issued Dec. 22, 1992, there is no suggestion in that application that the compounds of the present invention have superior neurotransmitter releasing profiles, as measured in an in vitro release, or an unexpectedly good dosage profile as measured by hypoxia-induced cognition impairment.

SUMMARY OF THE INVENTION

According to the present invention there is provided:
3-[4-(4-Pyridinylmethyl)-4H-indeno[1,2-B]thien-4-ylmethyl-pyridine;
Bis-4,4'-[4H-indeno[1,2-B]-thiophen-4-ylidene-bis(methylene)]-pyridine;
9,9-Bis(4-pyridinylmethyl)-9H-pyrrolo[1,2-A]indole;
or a pharmaceutically acceptable salt thereof.

Also provided are pharmaceutical compositions containing the aforesaid compound and methods of using them to treat neurological disorders.

DETAILED DESCRIPTION OF THE INVENTION

The compounds of this invention can be prepared by any of the general synthesis procedures described in U.S. Pat. No. 5,173,489.

The procedures described below represent modifications of the previously disclosed procedures for the syntheses of the title compounds.

The following examples are meant to be illustrative of the present invention. These examples are presented to exemplify the invention and are not to be construed as limiting the invention's scope.

EXAMPLE 1

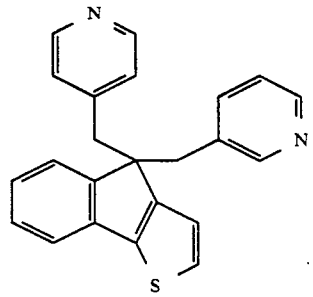

3-[4-(4-Pyridinylmethyl)-4H-indeno[1,2-Blthien-4-ylmethyl-pyridine dihydrochloride

Step 1

A 500 ml three-neck round bottom flask was charged with zinc chloride (75 ml, 1.0M in Et$_2$O) and cooled to 0° C. A solution of 2-thienyllithium (75 ml, 1.0M in THF) was added via dropping funnel over a 30 min period. The biphasic solution was stirred for an additional hour, transferred via cannula to a solution of methyl 2-iodobenzoate (13.1 g, 0.05 mole), tetrakis(triphenylphosphine) palladium (2.9 g, 0.0025 mole) in THF (120 ml) and allowed to stir at room temperature overnight. Water (500 ml) was added, and the resulting emulsion was filter through Celite. The organic phase was separated, and the aqueous phase was extracted with EtOAc (1×500 ml, 2×250 ml). The combined EtOAc extract was washed with brine, dried over Na$_2$SO$_4$, filtered, then further dried over MgSO$_4$. Following filtration and concentration, the crude ester was directly saponified with KOH (5.61 g, 0.10 mole), water (16.5 ml) and EtOH (65 ml) at reflux for one hour. The reaction was concentrated at 30° C., diluted with water (200 ml), washed with EtOAc (3×50 ml), Et$_2$O (1×50 ml) and the aqueous layer was filtered through Celite. The aqueous layer was acidified with conc. HCl and extracted with EtOAc (3×100 ml). The organic layer was washed with brine, dried over MgSO$_4$, filtered, concentrated and azeotroped with benzene. The resulting brown oil was refrigerated overnight to render intermediate I (10.0 g) in quantitative yield.

Step 2

The intermediate I prepared in Step 1 was dissolved in benzene (113 ml) and treated at room temperature with oxalyl chloride (4.7 ml, 0.053 mole) and catalytic N,N-dimethylformamide. Following stirring for 1 hour the reaction was evaporated "in vacuo". The residue was redissolved in benzene (113 ml) at 4° C. and tin (IV)

chloride (5.7 ml, 0.053 mole) was added. The reaction was stirred for 15 minutes (min) (or until complete as judged by tlc), quenched with water and 1N HCl until homogeneous and extracted with Et$_2$O. The Et$_2$O extract was worked up in the usual manner and the crude product was purified on silica gel using 5/1 hexane/ether to give intermediate II (5.8 g) in 58% yield; mp 99°–100° C.

Variations of the above procedures include the use of 2-trimethylstannyl thiophene instead of 2-thienyllithium/zinc chloride in Step 1, and the use of thionyl chloride instead of oxalyl chloride to form the acid chloride in Step 2.

Step 3

A solution of intermediate II from Step 2 (1.28 g) was allowed to heat in diethylene glycol at 160° C. before addition of hydrazine (13.9 ml) and elevation of temperature to 200° C. for 40 min. Upon cooling and dilution with water, followed by extractive isolation with Et$_2$O, a brown solid was isolated in quantitative yield; mp 62°–64° C.

Step 4

A solution of the product from Step 4 (1.87 g, 0.011 mole) was reacted with 4-pyridine carboxaldehyde (1.05 ml, 0.011 mole), KO$^t$Bu (1.35 g, 0.012 mole) in THF (40 ml) for 5 min. The reaction was quenched with saturated NH$_4$Cl (100 ml) amd extracted with CH$_2$Cl$_2$ (3×50 ml). The combined CH$_2$Cl$_2$ extract was washed with additional NH$_4$Cl, dried over MgSO$_4$. Upon concentration in vacuo, the crude red oil was reacted with zinc (11.0 g) in AcOH (50 ml) at reflux. Normal neutralization and extractive work up gave intermediate III as a solid in 75% yield; mp 91°–93° C. (hexane/ethyl acetate).

Step 5

To a solution of intermediate III from Step 4 (1 equiv.), 18-crown-6 (0.1 equiv.) in THF (50 ml per 2 mmol) was added at 0° C. potassium hexamethyldisilazide (1 equiv.) followed by stirring for 45 min. 3-Picolyl chloride hydrochloride (free based using potassium carbonate/water and extracted into toluene) (1 equiv.) was added and the reaction was stirred at room temperature overnight. The reaction was quenched in CHCl$_3$/satd. NH$_4$Cl (50 ml each). Following further extraction with CHCl$_3$, the combined CHCl$_3$ extract was washed with brine, dried over MgSO$_4$, filtered and concentrated. The crude residue was purified by column chromatography on silica gel using MeOH/CHCl$_3$ to give the free base. Characterization was by way of the mineral acid salt (HCl); the desired product (C$_{23}$H$_{18}$N$_2$S 2HCl) was obtained in 65% yield; mp. 237° C. dec.

EXAMPLE 2

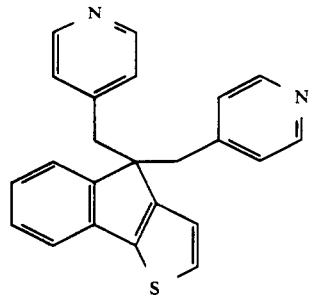

Bis-4,4'-[4H-indeno[1,2-b]-thiopen-4-ylidene-bis(methylene)]-pyridine

A solution of the product from Step 3, Example 1 (1.05 g, 6.1 mmol) in dimethyl sulfoxide (DMSO) (10 ml) was added dropwise to a mixture of KO$^t$Bu (1.44 g, 12.8 mmol) in DMSO/Et$_2$O (20 ml, 1:1) at 10° C. while stirring under dry nitrogen. The mixture was treated dropwise over 30 min with a solution of 4-picolyl chloride hydrochloride (free based) (14.6 mmol) in Et$_2$O (30 ml). The mixture was stirred at room temperature for 16 hr and poured into water (100 ml). The mixture was extracted with Et$_2$O (100 ml). The extract was washed with water and brine, dried over MgSO$_4$, filtered, and concentrated in vacuo to a foam (1.8 g). The foamed was column chromatographed on silica gel using CH$_2$Cl$_2$ as mobile phase. Appropriate fractions were combined and concentrated in vacuo. The residue was recrystallized from EtOAc/hexanes to give the desired product in 49% (1.06 g) yield; mp 144°–146° C.; Anal calcd for C$_{23}$H$_{18}$N$_2$S: C, 77.93; H, 5.12; N, 7.90. Found: C, 77.76; H, 4.89; N, 7.89. Mass spec m/e 355(M+1).

EXAMPLE 3

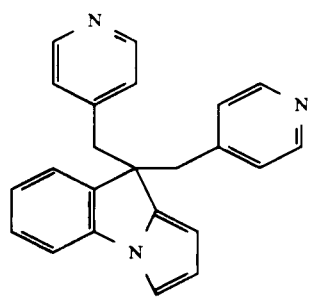

9,9-Bis(4-pyridinylmethyl)-9H-pyrrolo[1,2-a]indole

The starting material, 9H-Pyrrolo[1,2a]indole was prepared by the method described by Mazzola, V. J., et. al.; J. Org. Chem., 1967, 32, 486, and used in an anologous manner to that described in Example 2 to give the desired product as a solid, mp 107°–109° C.; Analysis calcd for C$_{23}$H$_{19}$N$_3$; C, 81.87; H, 5.68; N, 12.45. Found: C, 81.57; H, 5.57; N, 12.36. Mass spec m/e 338(M+1).

UTILITY

Biochemical Test Procedure

Neurotransmitter Release Assay

The neurotransmitter release activities of the compounds of this invention were determined as reported by Nickolson, et. al., Drug Development Research, 1990, 19, 285-300, as a modification of the procedure described by Mulder, et al., Brain Res., 1974, 70, 372. The in vitro release data is summarized in Table I.

Behavioral Test Procedure

Rat Passive Avoidance (PA) Hypoxia Induced Amnesia

Unfasted male CD rats, weighing between 165-210 grams, were trained in a PA apparatus using the following procedure: rats were placed in the clear side of the two compartment chamber and allowed 90 seconds to enter the dark compartment. Ten seconds after entering the dark chamber, a 3 second footshock (1.0 mA) was applied to the grid floor followed by an additional 10 second delay, and another 3 second footshock was applied. Retentions were tested 4 hours later. The rats were allowed 300 seconds to enter the dark compartment; time was taken. Memory disruption was induced by exposing the rats to a gas mixture containing 6.5% oxygen supplemented with nitrogen for 30 minutes before passive avoidance training. Doses of the test compound were administered (0.1 ml/100 g, sc.) relative to time of PA training.

Representative compounds of this invention were tested in the rat passive avoidance (PA) hypoxia induced amnesia model and found to be effective in diminishing the memory disruption caused by hypoxia. These results are shown in Table I.

TABLE I

| Ex. | Activity: % ACh Release | | PA Hypoxia: |
|---|---|---|---|
| | @ 1 μM | @ 10 μM | (sc) |
| 2 | 290 | 436 | Active |
| 1 | — | 198 | — |
| 3 | 124 | 282 | Active |

The foregoing test results establish that the compounds of this invention can have utility in the treatment of cognitive and neurological disorders with high efficacy and a wide safety margin. The compounds of this invention can be administered to treat said deficiencies by any means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Anti-oxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences". A. Osol, a standard reference in this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil was prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed absorption.

The compounds of this invention may also be used as reagents or standards in the biochemical study of neurological function, dysfunction, and disease.

What is claimed is :

1. A compound selected from the group consisting essentially of 3-4-(4-Pyridinylmethyl)-4H- indeno[1,2-B]thien-4-ylmethyl-pyridine dihydrochloride; Bis-4,4'-[4H- indeno[1,2-B]-thiophen-4-ylidene-bis-(methylene)-pyridine; and 9,9-Bis(4-pyridinylmethyl)-9H-pyrrolo[1,2-A]indole, or a pharmaceutically acceptable salt thereof.

2. A compound of claim 1 which is 3-[4-(4-Pyridinylmethyl)-4H-indeno[1,2-B]thien-4-ylmethyl-pyridine dihydrochloride, or a pharmaceutically acceptable salt thereof.

3. A compound of claim 1 which is Bis-4,4'-[4H-indeno[1,2-B]-thiophen-4-ylidene-bis-(methylene)]-pyridine, or a pharmaceutically acceptable salt thereof.

4. A compound of claim 1 which is 9,9-Bis(4-pyridinylmethyl)-9H-pyrrolo[1,2-A]indole, or a pharmaceutically acceptable salt thereof.

5. A pharmaceutical composition consisting essentially of a pharmaceutically suitable carrier and an effective amount of the compound of claim 1.

6. A pharmaceutical composition consisting essentially of a pharmaceutically suitable carrier and an effective amount of the compound of claim 2.

7. A pharmaceutical composition consisting essentially of a pharmaceutically suitable carrier and an effective amount of the compound of claim 3.

8. A pharmaceutical composition consisting essentially of a pharmaceutically suitable carrier and an effective amount of the compound of claim 4.

9. A method of treating a neurological disorder in a mammal comprising: administering to the mammal an effective amount of the compound of claim 1.

10. A method of treating a neurological disorder in a mammal comprising: administering to the mammal an effective amount of the compound of claim 2.

11. A method of treating a neurological disorder in a mammal comprising: administering to the mammal an effective amount of the compound of claim 3.

12. A method of treating a neurological disorder in a mammal comprising: administering to the mammal an effective amount of the compound of claim 1.

* * * * *